United States Patent
Sargolzaei et al.

(10) Patent No.: US 10,349,859 B2
(45) Date of Patent: Jul. 16, 2019

(54) SIMULATION AND DIAGNOSTIC TOOL FOR SENSORIMOTOR DISEASES

(71) Applicants: Arman Sargolzaei, Miami, FL (US); Mohamed Abdelghani, Greenville, SC (US); Kang K. Yen, Miami, FL (US); Saman Sargolzaei, Miami, FL (US)

(72) Inventors: Arman Sargolzaei, Miami, FL (US); Mohamed Abdelghani, Greenville, SC (US); Kang K. Yen, Miami, FL (US); Saman Sargolzaei, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 12 days.

(21) Appl. No.: 15/622,953

(22) Filed: Jun. 14, 2017

(65) Prior Publication Data

US 2018/0360339 A1  Dec. 20, 2018

(51) Int. Cl.
*A61B 5/00* (2006.01)
*G06F 19/00* (2018.01)
*A61B 5/0476* (2006.01)
*G16H 30/00* (2018.01)

(52) U.S. Cl.
CPC .......... *A61B 5/0476* (2013.01); *A61B 5/6868* (2013.01); *A61B 5/7246* (2013.01); *G06F 19/34* (2013.01); *G16H 30/00* (2018.01)

(58) Field of Classification Search
None
See application file for complete search history.

(56) References Cited

PUBLICATIONS

Guenther, F. H., Ghosh, S. S., & Tourville, J. A. (2006). Neural modeling and imaging of the cortical interactions underlying syllable production. Brain and language, 96(3), 280-301. (Year: 2006).*
Robinson et al., "A model of the smooth pursuit eye movement system," Biological Cybernetics, Oct. 1986, pp. 43-57, vol. 55.
Abaspour et al., "Nonlinear optimized adaptive trajectory control of helicopter," Control Theory and Technology, Nov. 2015, pp. 297-310, vol. 13, No. 4.
Abaspour et al., "A new feedback linearization-NSGA-II based control design for PEM fuel cell," International Journal of Computer Applications, Jul. 2014, pp. 25-32, vol. 97, No. 10.
Abaspour et al., "Using fuzzy logic in dynamic inversion flight controller with considering uncertainties," 13th Iranian conference on Fuzzy Systems (IFSC), Aug. 27-29, 2013, pp. 1-6.
Abdelghani et al., "Sensitivity derivatives for flexible sensorimotor learning," Neural Computation, Aug. 2008, pp. 2085-2111, vol. 20, No. 8.

(Continued)

*Primary Examiner* — Bijan Mapar
(74) *Attorney, Agent, or Firm* — Saliwanchik, Lloyd & Eisenschenk (57) ABSTRACT

Computational models and methods and systems of using the model to estimate variable time delay in the sensorimotor system of a subject are provided. The computational model can estimate variable time delays in the sensorimotor system, predict sensory states based on delayed sensory feedback, and/or control the system in real time. The subject can be a human or a primate. Simulation experiments can show how the model can explain a sensorimotor system's ability to compensate for delays during online learning and control.

17 Claims, 4 Drawing Sheets

(56) References Cited

PUBLICATIONS

Abdelghani et al., "Learning course adjustments during arm movements with reversed sensitivity derivatives," BMC Neuroscience, Nov. 2010, pp. 1-10, vol. 11, No. 150.
Aw et al., "Latency and initiation of the human vestibuloocular reflex to pulsed galvanic stimulation," Journal of Neurophysiology, Aug. 2006, pp. 925-930, vol. 96.
Churchland et al., "Apparent motion produces multiple deficits in visually guided smooth pursuit eye movements of monkeys," Journal of Neurophysiology, Jul. 2000, pp. 216-235, vol. 84.
Dallos et al., "Learning behavior of the eye fixation control system," IEEE Transactions on Automatic Control, Jul. 1963, pp. 218-227.
Franklin et al., "Computational mechanisms of sensorimotor control," Neuron, Nov. 2011, pp. 425-442, vol. 72, No. 3.
Ito et al., "Fast force-generation dynamics of human articulatory muscles," Journal of Applied Physiology, Jun. 2004, pp. 2318-2324, vol. 96.
Kheradmand et al., "Cerebellum and ocular motor control," Frontiers in Neurology, Sep. 2011, pp. 1-15, vol. 2, No. 53.
Koelewijn et al., "Resting-state oscillatory dynamics in sensorimotor cortex in benign epilepsy with centro-temporal spikes and typical brain development," Human Brain Mapping, Jul. 2015, pp. 3935-3949, vol. 36.
Matthews, "The human stretch reflex and the motor cortex," Trends in Neurosciences, Mar. 1991, pp. 87-91, vol. 14, No. 3.
Miall et al., "Disruption of state estimation in the human lateral cerebellum," PLOS Biology, Nov. 2007, pp. 2733-2744, vol. 5, No. 11.
Muller et al., "Estimation of delay times in biological systems," Annals of Biomedical Engineering, Dec. 2003, pp. 1423-1439, vol. 31, No. 11.
Sargolzaei et al., "Preventing time-delay switch attack on load frequency control in distributed power systems," IEEE Transactions on Smart Grid, Mar. 2016, pp. 1176-1185, vol. 7, No. 2.
Sargolzaei et al., "Control of nonlinear heartbeat models under time-delay-switched feedback using emotional learning control," International Journal on Recent Trends in Engineering and Technology, Jan. 2014, pp. 85-91, vol. 10, No. 2.
Shibata et al., "A model of smooth pursuit in primates based on learning the target dynamics," Neural Networks, Mar. 2005, pp. 213-224, vol. 18.
Takarae et al., "Visual motion processing and visual sensorimotor control in autism," Journal of the International Neuropsychological Society, Jan. 2014, pp. 113-122, vol. 20.
Todorov et al., "Optimal feedback control as a theory of motor coordination," Nature Neuroscience, Nov. 2002, pp. 1226-1235, vol. 5, No. 11.
Holm et al., "Bias in the cross spectrum and time delay estimates due to misalignment," IEEE Transactions on Acoustics, Speech, and Signal Processing, Dec. 1986, pp. 1662-1665, vol. 34, No. 6.
Raibert, "A model for sensorimotor control and learning," Biological Cybernetics, Mar. 1978, pp. 29-36, vol. 29.
Stark et al., "Predictive control of eye tracking movements," IRE Transactions on Human Factors in Electronics, Sep. 1962, pp. 52-57.
Cleveland et al., "The estimation of coherence, frequency response, and envelope delay," Technometrics, May 1975, pp. 167-172, vol. 17, No. 2.
Carter, "Coherence and time delay estimation," Proceedings of the IEEE, Feb. 1987, pp. 236-255, vol. 75, No. 2.
Hinich et al., "Time delay estimation using the cross bispectrum," IEEE Transactions on Signal Processing, Jan. 1992, pp. 106-113, vol. 40, No. 1.
Cabot, "A note on the application of the hilbert transform to time delay estimation," IEEE Transactions on Acoustics, Speech, and Signal Processing, Jun. 1981, pp. 607-609, vol. ASSP-29, No. 3.
Chan et al., "The least squares estimation of time delay and its use in signal detection," IEEE Transactions on Acoustics, Speech, and Signal Processing, Jun. 1978, pp. 217-222, vol. ASSP-26, No. 3.
Sargolzaei et al., "Delayed inputs attack on load frequency control in smart grid," Innovative Smart Grid Technologies Conference (ISGT) Feb. 19-22, 2014, pp. 1-5.

\* cited by examiner

SIMULATION AND DIAGNOSTIC TOOL FOR SENSORIMOTOR DISEASES

BACKGROUND

The brain's sensorimotor cortex, as a complex neural sensorimotor control system, inherently finds and accomplishes all of its tasks in an optimal manner in terms of speed, accuracy, and efficiency in a vast range of input conditions [3, 4]. Noises, nonlinearities, delays, uncertainties, and redundancies are among many major problems that a sensorimotor control system may experience [5].

A primate's sensorimotor controller is equipped with the ability to predict motor movements and to compensate for time delays. Time-delay estimation is a difficult problem to simulate because it renders even the simplest linear systems nonlinear; yet, biological control systems are robust enough to deal with time delays. It is unclear, however, how this is achieved in biological systems.

For example, vestibulo-ocular reflex (VOR), a motor control system that stabilizes vision during head movements, is not prone to occurrence of delay up to 10 milliseconds from the onset of stimulus [8]. Smooth pursuit, another efficient visual control system in humans for target tracking in the visual field, has the ability to process information with an 80-130 millisecond delay in the brain [25, 26]. Delays make control difficult because information about the current state of the motor system is outdated. A motor control system that does not have delay compensation mechanisms could not correct for errors, leading to potential inefficiencies and instability.

Currently available time-delay estimation techniques mainly cover linear systems including, for example, constant time delays, random time delay with specific noise characteristics, and restricted dynamic time delay [20-27]. Most biological systems, however, exhibit some degree of variability, nonlinearity, and uncertainty, which can render these methods inapplicable. Further, most delay estimation procedures are not used in the context of predictive control methodology. The Hilbert-Huang Transform-based method, for example, is found to be the most efficient delay estimation technique with a focus on practical applicability to the motor control. However, the process is a complex one [26]. As such, a comprehensive and predictive computational model to explain time-delay compensation in biological control is still lacking.

BRIEF SUMMARY

Embodiments of the subject invention provide computational models and methods of using the same to estimate variable time delay in the sensorimotor system of a subject.

In some embodiments, the computational model can accomplish one or more of the following tasks: estimating variable time delays in the sensorimotor system; predicting sensory states based on delayed sensory feedback; and controlling the system in real time. Embodiments provide that the subject is a human or a primate.

In some embodiments, simulation experiments are used to show how the models provided herein can explain a sensorimotor system's ability to compensate for delays during online learning and control. Specifically, examples are provided to demonstrate the benefits of the time-delay estimation model and the application of the model to simulate a horizontal Vestibulo-Ocular Reflex (hVOR) system.

Systems, methods, and models provided herein are distinguished from prior art methods in that prior art computational models are only capable of simulating a sensorimotor control system in the presence of time delays and noise rather than predicting the dynamics of variable time delays and future sensory states from delayed sensory information.

Advantageously, systems, models, and methods provided herein can lead to a better understanding of the function of the human sensorimotor cortex, with practical applications in explaining the mechanisms underlying neurological disorders manifested as delays and faults affecting the brain (e.g., autism [28], Parkinson's disease, Alzheimer's disease, epilepsy [29]) and the eye. Further, the technology provided herein can be used to model behavior of a healthy sensorimotor system (e.g., parts or whole of a healthy brain) based on faulty information received from the system's neurons.

DETAILED DESCRIPTION

Embodiments of the subject invention provide computational models and methods and systems of using the models to predict the dynamics of variable time delays and future sensory states from delayed sensory information.

The term "subject", in the context of a subject being tested, examined, or the like, can refer to a human or a primate such as, for example, a baboon, a monkey, or a macaque.

In some embodiments, a "sensorimotor system" can be a combination of at least one sensory organ, associated muscle or muscle groups, and neural networks that control the organs and the muscles to accomplish a desired motion or task. Non-limiting examples of sensory organs include those that are capable of performing ophthalmoception (sight), audioception (hearing), gustaoception (taste), olfacoception (smell), and/or tactioception (touch), such as, e.g., eyes, ears, sensors in the head for vibration and proprioception; such organs can be monitored with, for example, blood pressure sensors, glucose sensors, temperatures sensors, and external vibration sensors.

In some embodiments of the subject invention, a sensorimotor system can execute one or more of the following processes: horizontal vestibule-ocular reflex, saccadic eye movement, smooth pursuit system, hand movements, hand-eye coordination, walking, running, skilled movements, opto-kinetic reflex, and balance tasks.

For a primate or a human subject, time delays can occur in various parts of the sensorimotor system. The value of time delay is dynamic and can vary with each specific sensory modality. The complexity of processing sensory information further depends on the nature of the task. For example, because there is a longer delay for vision than for proprioception, face recognition takes longer than motion perception.

Due to delays in information processing and transmission, simple feedback control is affected by significant temporal discrepancies between the target signal and the current state, suggesting that some form of predictive control must take place to achieve such a high performance in the system [15].

For example, the duration of saccadic eye movement, a fast eye movement produced by a visual system that directs the eyes to interesting visual stimuli, is shorter than the sensory delay [25]. This means that the sensory feedback about the current state of the eye and the visual field cannot be used to correct or guide the saccades because the sensory information regarding the movement itself arrives after the completion of the movement.

In a further example, the smooth pursuit eye movement allows a human subject to track targets in the visual field at a high speed of approximately 200° (degrees of field of vision) per second. However, the position of the eyes is ahead of the visual sensory feedback of the target position. As a result, this phenomenon cannot be achieved by solely implementing standard negative feedback methods based on visual error signals [12-14].

Primates have demonstrated this predictive nature of sensorimotor control systems in prior art experiments. For example, monkeys have the ability to conduct smooth pursuit movements with zero retinal slip [16, 17] and maintain smooth pursuit during blink periods (i.e., momentary disappearances of the target) [18]. Such predictive compensation was observed both in tracking moving targets with constant velocity or in sinusoidal moving objects. In a hand movement study, it was demonstrated that the cerebellum is involved in predicting the position of the hand during a movement [19]. The predicted state of the limb from the history of motor commands allows the motor control to act on this estimate of state rather than relying solely on a delayed sensory feedback. This suggests that cerebellar output is a signal that can be combined with delayed sensory feedback elsewhere in the brain in order to generate estimates of real-time states of motor control.

Embodiments of the subject invention address the above-mentioned need for estimating time delays and predicting control solutions in a subject's sensorimotor system by providing a computational model that can be evaluated in real time, with online learning and control simulation processes.

In some embodiments, a computational model simulates a subject's brain as a sensorimotor control system and can accomplish one or more of the following tasks: 1) estimating variable time delay in the sensorimotor system; 2) predicting sensory states based on delayed sensory feedback; and 3) controlling the system in real time.

In order for the model to simulate the brain as a sensorimotor system, the following assumptions are incorporated herein: 1) the brain possesses a time-delay estimator circuit; 2) the brain uses the estimate of time delay to predict the current state; 3) the brain uses the current predicted estimate to control motor movements; and 4) the brain is a truly autonomous system and that it does not maintain an absolute time, but only what is perceived from external, periodic stimuli.

Figure 1:
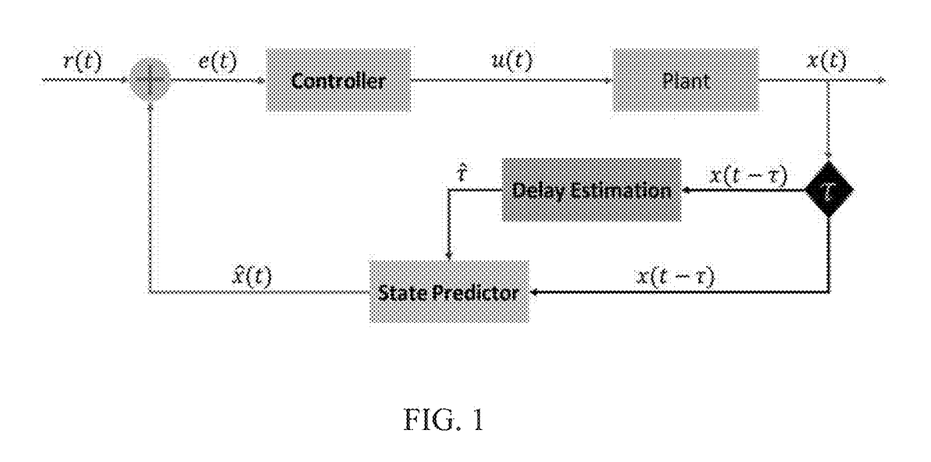
FIG. 1 is a model of sensorimotor control with time-delay estimation and sensory states predictor. The Plant symbolizes a higher level of a sensorimotor system such as the eye, associated muscles, sensors, responses, goals, and objectives (e.g., minimize retinal slip in Vestibulo-Ocular Reflex (VOR)). The Controller is the neural network responsible for achieving the required task in an "optimal" way. The Delay Estimator is a circuit that can function as a "brain", according to an embodiment of the subject invention, or a sensorimotor system to estimate time delay in a sensory and motor pathway. State Predictor is where current and "future" sensory states are estimated and predicted, respectively, based on the estimated current time delay. The "r(t)" is the desired goal, or in the language of control theory, the reference trajectory. The "e(t)" is the error difference between the desired sensory state and predicted sensory state $\hat{x}(t)$. The "u(t)" are the motor commands to muscles or effector organs. The "x(t−τ)" are the delayed sensory states. The "x(t)" is the actual sensory state. Finally, "τ" is the time delay that could either be a natural time delay or a consequence of damage or disease.

Referring to FIG. 1, in an embodiment, elements and connectivity between components of the computational model simulating the brain as a sensorimotor control system at a higher level can be as shown. Tables 1 and 2 explain each known and unknown variable of FIG. 1. Note that the "Delay Estimator," the "State Predictor," and the "Controller" represent the three tasks the model aims to accomplish and is each described in detail herein.

TABLE 1

Sensorimotor control known variables

| Variable | Definition |
| --- | --- |
| r(t) | Goal or reference |
| x(t − τ) | Delayed sensory inputs |
| ê(t) | Prediction errors |
| $\hat{\tau}$ | Estimated time delay |
| G(t − $\hat{\tau}$) | Estimated sensory Jacobian |
| B | Control Jacobian |
| u | Motor commands |

TABLE 2

Sensorimotor control unknown variable

| Variable | Definition |
| --- | --- |
| τ(t) | Real time delay |
| x(t) | Current sensorimotor state |

Estimating the Time Delay

As provided herein, a sensorimotor system (e.g., the brain) can be approximated in a region of interest by a linear time-varying system, as stated in Equation (1):

$$\dot{x}(t) = A(t)x(t) + B(t)u(t) \quad (1)$$

where x(t) is the state vector (e.g., the position of the eye or hand in space, etc.), u(t) is the control vector or the neural motor commands (e.g., the firing of motor-neurons or muscle contractions), and A(t) and B(t) are time-varying matrices with appropriate dimensions. Also, r(t) is desired sensory outcome, x(t) represents current sensory state, and u(t) represents motor commands that try to bring current sensory state to desired sensory outcome.

Jacobian matrix A(t) represents the influence of the current state x(t) of the motor system to its future changes $\dot{x}(t)$. Jacobian matrix B(t) is the sensorimotor controller gain, which determines how motor commands affect $\dot{x}(t)$. In some embodiments, A(t) and B(t) can change over time. Non-limiting examples representing A(t) and B(t) include joint friction, viscosity, and elasticity of muscles, which can all change over time. A(t), G(t), B(t), and u(t) can be inferred or computed from sensory inputs; in simulation of a sensorimotor system, these matrices can instead be inferred from measured sensory signals.

The solution to the first order differential Equation (1) is given by $$x(t) = e^{\int_0^t A(s)ds}x_0 + \int_0^t e^{\int_s^t A(v)dv}B(s)u(s)ds \qquad (2)$$

where $x_0$ is the initial state [30].

Let $G(t)=e^{\int_0^t A(s)ds}$ and Equation (2) written in terms of G(t) is $$x(t) = G(t)x_0 + G(t)\int_0^t G^{-1}(s)B(s)u(s)ds \qquad (3)$$

where x(t) is the current state of the sensorimotor system measured by the sensor organs. The motor command vector is u(t).

Motor commands are usually sensed at the level of the effector by specialized sensory organs. In an embodiment, muscle spindles can measure the force generated in the muscle and communicate the information to the brain. As a result, it is assumed that x(t) and u(t) can be precisely measured by sensory organs represented by the "Plant" box as shown in FIG. 1.

As provided herein, the sensory time-delay vector is represented by $\tau=[\tau_i]$ (i.e., the $i^{th}$ time delay value). In a preferred embodiment, it is assumed that $\tau=\tau_i$ hereafter. The solution of Equation (2) incorporating the time delay is thus $$x(t-\tau) = G(t-\tau)x_0 + G(t-\tau)\int_0^{t-\tau} G^{-1}(s)B(s)u(s)ds \qquad (4)$$

As an autonomous system, the brain perceives the sensation of time based on external periodic stimulation. In other words, the brain is a data-driven asynchronous collection of sensorimotor control systems. This feature distinguishes the brain from industrial control systems, which utilize synchronized clocks to count the ticking of time. As a result, the time variable t can be accessed directly in an industrial control system but not in the brain's sensorimotor control system.

The brain keeps an internal estimate of time delays, denoted as $\hat{\tau}$, and is capable of using the estimated time delay to predict the current and future sensory states. The error signal between the delayed sensory signal x(t−τ) and the estimated delayed sensory signal x(t−$\hat{\tau}$) is calculated as (=x(t−τ)−x(t−$\hat{\tau}$). The delayed sensory signals are known to the brain, but the brain cannot access the time delay vector τ directly. On the other hand, x(t−$\hat{\tau}$) is unknown since $\hat{\tau}$ is unknown. One skilled in the art would appreciate that the delayed sensory signal x(t−τ) can in fact be computed from the knowledge of G(t), B(t) and u(t) as provided by the model of the subject invention.

To compute $\hat{\tau}$, a modified version of the gradient descends method is used:

$$\frac{d\hat{\tau}}{dt} = -\eta \zeta \frac{\partial \zeta}{\partial \hat{\tau}} \qquad (5)$$

where η is the learning parameter that represents how fast and effectively a person can learn; this parameter can be learned by neural mechanisms or programmed genetically, and it indicates how fast the synapses can adjust their strength. In simulation learning, it can be measured from the subject via experiments and programmed in a simulation system.

Using Equation (3), Equation (5) can then be written in a meaningful form as shown below $$\frac{d\hat{\tau}}{dt} = -\eta\zeta\frac{\partial[x(t-\tau)-x(t-\hat{\tau})]}{\partial\hat{\tau}} = \eta e_m \frac{\partial x(t-\hat{\tau})}{\partial \hat{\tau}} \qquad (6)$$
$$= \eta\zeta\frac{\partial G(t-\hat{\tau})}{\partial \hat{\tau}}\left[x_0 + \int_0^{t-\hat{\tau}}(B(s)/G(s))u(s)ds\right] -$$
$$\eta\zeta\{B(t-\hat{\tau})u(t-\hat{\tau}) - G(t-\hat{\tau})B(0)u(0)\}$$

While the time delay τ can be estimated using Equation (6), there are biological constraints that need to be considered. For example, Equation (6) requires the knowledge of x(t−$\hat{\tau}$), G(t−$\hat{\tau}$) and u for any 0≤$\hat{\tau}$≤t−τ. But, this is impossible because it needs to store the full history of motor commands u(t) or all functions including G(t) and x(t). Therefore, assuming the biological plausibility of Equation (6) without boundedness assumptions on the maximum delay τ is not possible.

Thus, in order to guarantee stability and limit memory usage, the condition $\tau \leq \tau_{max}$ is added, where $\tau_{max}$ is the maximum possible delay after which the system becomes inoperable. This condition does not limit the generality of the method provided herein. Furthermore, this condition is reasonable because most human movements are either repetitive, e.g., walking, or intermittent with many pauses, e.g., reaching. In reaching, for example, at the beginning of the movement, the initial position of the arm is known, and the delay is not an issue because the arm is at rest. At the end of the movement, the arm is coming back to rest and the final state of the arm is known. Therefore, delays have no detrimental effects. However, during motion, the state of the arm keeps changing which causes the values communicated to the brain affected by variable delays. It is during the arm's motion that the delay estimation is paramount. Since movements are finite in time, applying a limit on the maximum number of delays is also reasonably justified.

In some embodiments, the history of constructed signals can be stored in a finite buffer for the purpose of hardware implantation. Similarly, the brain automatically stores history of signals such as u(t) (motor commands) and x(t) (actual sensory state) by, for example, learning the dynamics of G(t) and B(t) and thereby computing the dynamics of x and u for any time period. If in a computer system, these quantities can be stored in, for example, a hard drive, RAM, or other computer-readable storage media. If in the brain, then they can be stored in, for example, a network of neurons and synapses.

In accordance with embodiments provided herein, it is assumed that the brain stores u(t) from t to t−$\tau_{max}$, as well as G(t), B(t) and x. In the case that the time delay exceeds $\tau_{max}$, a complete open-loop control prevails.

Predicting Current and Future Sensory States

Advantageously, the model provided herein can simulate and explain the predictive nature of a primate subject's sensorimotor system as demonstrated by, for example, the smooth pursuit system and the ability to compensate for long delays. In some embodiments, the model can also predict the future state of a sensorimotor system based on the system's delayed state and an estimate of the time delay using Equation (6) and boundary conditions provided herein. Specifically, by combining Equations (3) and (4) as follows $$x(t) = G(t)G^{-1}(t-\tau)x(t-\tau) + G(t)\int_{t-\tau}^{t} B(s)G^{-1}(s)u(s)ds. \quad (7)$$

the future state can be predicted using the time-delay estimate $\hat{\tau}$ $$\hat{x}(t) = G(t)G^{-1}(t-\hat{\tau})x(t-\hat{\tau}) + G(t)\int_{t-\hat{\tau}}^{t} B(s)G^{-1}(s)u(s)ds. \quad (8)$$

Importantly, x(t−τ) is the variable that can be measured and delivered to the sensorimotor plant model in the brain, represented by Equation (4). However, G(t) and the integral over u(t) are both dependent on the estimate of the time delay $\hat{\tau}$. When the error in the estimate of time delay $\varepsilon = \hat{\tau} - \tau$ decreases to zero, the predicted state approaches to the actual state x(t).

The variable that represents motor commands, namely u(t), combines the sensorimotor plant model ("Plant" in FIG. 1) with the motor controller ("Controller" in FIG. 1). As provided herein, the plant model symbolizes a higher level of sensorimotor system. In the case of hVOR, the plant model includes the eye, associated muscles, sensor, responses, goals, and objectives (e.g., to minimize retinal sip).

In order to calculate u(t), the difference between the desired sensory goal r(t) and current state x(t), i.e., the performance error e(t)=r(t)−x(t) must be calculated first, and then the estimated performance error ê(t)=r(t)−x̂(t). Then, the proportional-integral-derivative (PID) controller input can be calculated in terms of the estimated error as [31, 32]:

$$u(t) = K_P \hat{e}(t) + K_D \frac{d\hat{e}(t)}{dt} + K_I \int_0^t \hat{e}(s)ds \quad (9)$$

and the optimal feedback controller as $$u(t) = K\hat{e}(t) \quad (10)$$

where $K_P$, $K_D$, $K_I$ and K are proportional gain, derivative gain, integral gain, and optimal gain, respectively.

The PID controller and the optimal feedback controller gains can be designed as if there was no delay with information about the predicted state. Because the controller depends on the estimated performance error ê(t) that results from the estimated current sensory state x̂(t), as the estimated x̂(t) converges to x(t), ê(t) converges to e(t).

In some embodiments, simulation experiments are used to show how the model can explain a sensorimotor system's ability to compensate for delays during online learning and control. Specifically, examples are provided to demonstrate the benefits of the time-delay estimation and prediction model and the application of the model to simulate a horizontal Vestibulo-Ocular Reflex (hVOR) system (see Example).

Figure 2A:
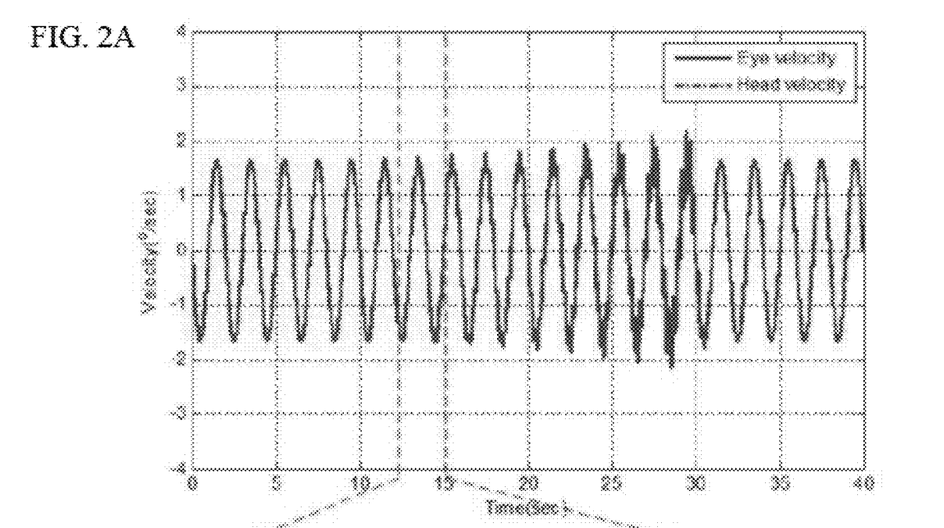
FIG. 2A is a plot of velocity versus time, demonstrating horizontal VOR (hVOR) performance with failed time-delay compensation.
Figure 2B:
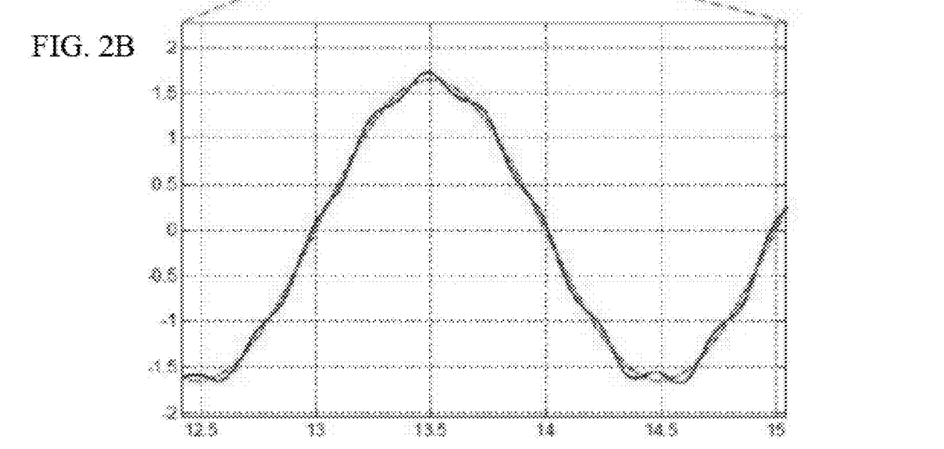
FIG. 2B is a blown-up section of the plot of FIG. 2A.

Importantly, without the time-delay estimate and sensory state predictor built into the model, the hVOR is unstable and can be affected by high frequency oscillations (see, for example, FIGS. 2A and 2B). Specifically, FIGS. 2A and 2B show a poor response of the eye rotation to head rotation with traditional controller. Because the eye is responding to a delayed head velocity, velocity of the eye (blue solid line) is oscillating around the head velocity (red dashed line) (FIG. 2B). This oscillatory behavior is as if the eye is executing a corrective movement (saccades) to compensate for the delayed head velocity. However, it often overshoots the target head velocity. This oscillatory behavior continues until the hVOR fails to do its job completely.

These oscillations are reminiscent of a fast correction mechanism, e.g., a saccade of events used to compensate for hVOR delays. This suggests that, on one hand, a hVOR system with impaired time-delay estimation and/or impaired sensory state predictor can mimic certain outcomes of sensorimotor diseases. On the other hand, if the control of a hVOR is augmented with the time-delay estimator and/or the predictor for eye position relative to the head as provided herein, the hVOR control is stable and smooth.

Behavior similar to that shown in FIGS. 2A and 2B could also be the result of a damaged sensory state predictor. In this case, even if the time-delay estimation is working properly the state predictors fails to predict the correct current state. As a result, the hVOR will be plagued with oscillations and instability. Thus, in some embodiments, the model provided herein can also be used to detect faulty sensorimotor systems resulted from neurological disorders affecting the brain or the eye. Non-limiting examples of neurological disorders affecting the brain include autism [28], Parkinson's disease, Alzheimer's disease, an epilepsy [29].

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

Advantageously, models, methods, and systems provided herein can lead to a better understanding of the function of the human sensorimotor cortex, with practical applications in explaining the mechanisms underlying neurological disorders manifested as delays and faults affecting the brain (e.g., autism [28], Parkinson's disease, Alzheimer's disease, epilepsy [29]) and the eye. Furthermore, the technology provided herein can be used to model behavior of a healthy sensorimotor system (e.g., parts or whole of a healthy brain) based on faulty information received from the system's neurons.

Figure 3A:
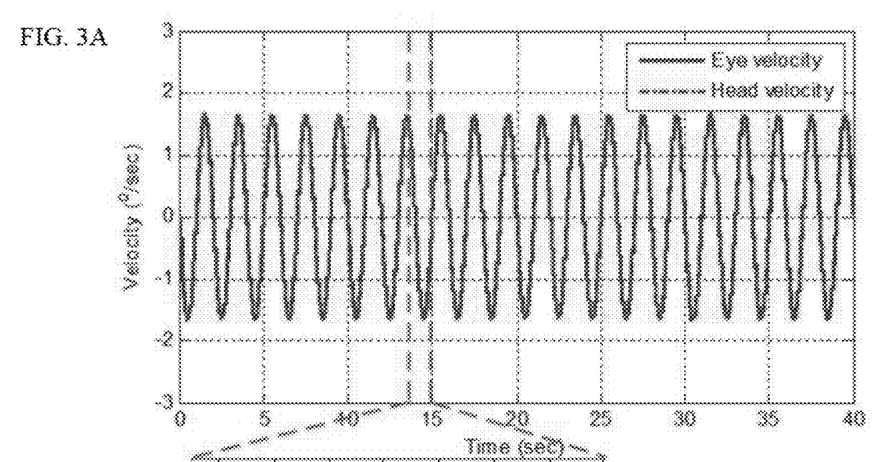
FIG. 3A is a plot of velocity versus time, demonstrating the hVOR performance with existence of time-delay estimator and state predictor under long time delay obtained using a method according to an embodiment of the subject invention. The eye velocity is the reverse of the head velocity.
Figure 3B:
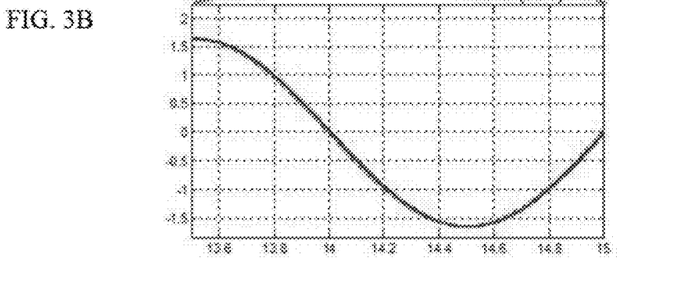
FIG. 3B is a blown-up section of the plot of FIG. 3A.

The models, methods, and systems provided herein can be used to address sensory brain diseases, such as the one explained in reference [34], which is hereby incorporated by reference herein in its entirety (see, e.g., FIG. 3 of Reference [34]). The results provided in the Example below are like real data for a patient with this disease. Also, models, methods, and systems provided herein can be used, for example, to implement a correction tool through eye glasses to help patients with eye diseases. A patient can wear a virtual glass set of eye glasses with capability of measuring eye movement and/or head movement and measure the amount of delay. Then, the measurement can be used to stimulate sensory neurons to make them faster, and such virtual reality eye glasses can be used to show images (e.g., coming from a camera) with delay to relieve patient problems.

A greater understanding of the present invention and of its many advantages may be had from the following example, given by way of illustration. The following example is illustrative of some of the methods, applications, embodiments and variants of the present invention. They are, of course, not to be considered as limiting the invention. Numerous changes and modifications can be made with respect to the invention.

Example 1

The time-delay estimation model provided herein was applied to simulate the vestibulo-ocular reflex (VOR) sensorimotor system. The model was implemented in MATLAB R2013a.

In the horizontal VOR (hVOR), $x \in \mathbb{R}$ is the eye position relative to the head, and $u \in \mathbb{R}$ is the net motor-neuron signal to the horizontal eye muscles. So, the hVOR system equation in its simplest form [1] is shown as:

$$\dot{x} = -\frac{\kappa}{\rho}x + \frac{1}{\rho}u \tag{11}$$

where $\kappa$ is the coefficient of viscosity and $\rho$ is the coefficient of elasticity, and both are constants. The retinal-image slip velocity is $y \in \mathbb{R}$, which is the sum of eye and head velocities, $$y = \dot{x} + h \tag{12}$$

The goal of the hVOR is to make the retinal slip equal to zero, i.e., $y=0$. Here, the reference signal $r$ is $r=-h$ and the feedback error signal is $e=x-r=x+h$. Therefore, $y=\dot{e}$ and the feedback control law is basically a derivative control given by $$u(t) = K_D \dot{e}(t) \tag{13}$$

Choosing the appropriate $K_D$ results in $\dot{e}=y=0$.

With sensory delay $\tau$, the measured state of the hVOR control system will be $x(t-\tau)$ instead of $x(t)$, which is a form of time-delay estimation and a plant state predictor.

Based on the model provided herein, the time-delay estimator can be written as $$\dot{\hat{\tau}} = \frac{\eta}{\rho}\zeta\left[e^{-(\kappa/\rho)(t-\hat{\tau})}\left(\rho x_0 + \int_0^{t-\hat{\tau}} e^{-(\kappa/\rho)(s-\hat{\tau})}u(s)ds\right)\right] - \frac{\eta}{\rho}\zeta u(t-\hat{\tau}) \tag{14}$$

where it is assumed that $u(0)=0$. The state predictor can be found as $$\hat{x}(t) = e^{(\kappa/\rho)\hat{\tau}}x(t-\tau) + \frac{e^{-(\kappa/\rho)t}}{\rho}\int_{t-\hat{\tau}}^t e^{(\kappa/\rho)s}u(s)ds \tag{15}$$

Without time-delay estimation and prediction, the hVOR is unstable and could be affected by high frequency oscillations (see, for example, FIGS. 2A and 2B). These oscillations are reminiscent of a fast correction mechanism, e.g., a saccade to compensate for hVOR delays [33].

Figure 4:
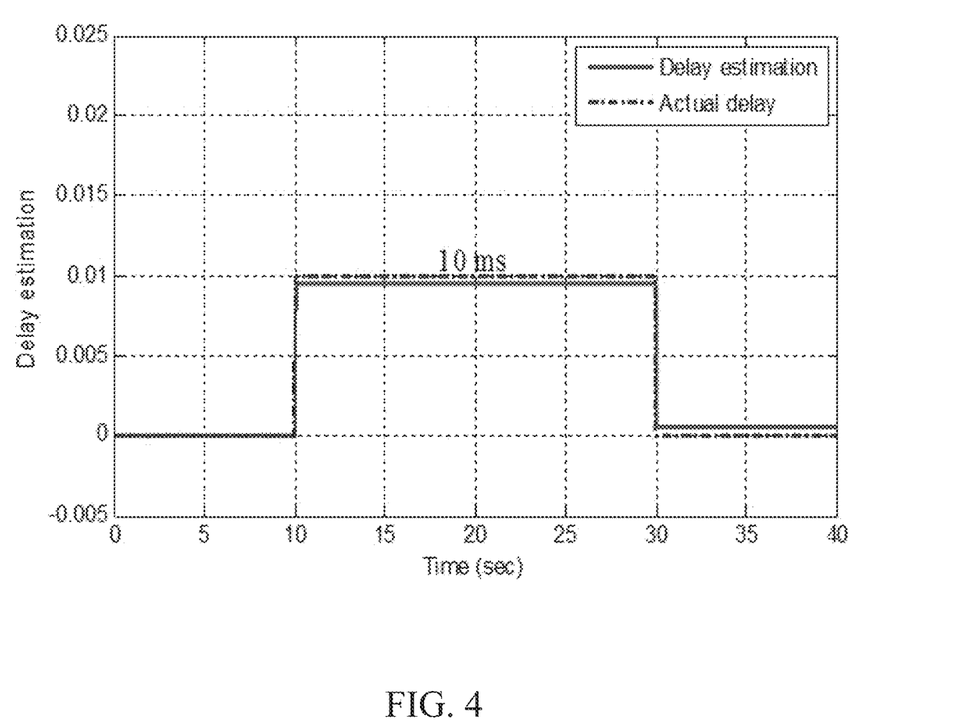
FIG. 4 is a plot of delay estimation versus time, showing the response of a time-delay estimation circuit for a hVOR system according to an embodiment of the subject invention. The blue dashed line is the variation of the time delay during horizontal head movement. The red solid line is the simulated tracking of the time-delay estimation circuit.

When compared with prior art findings [34], the simulation result shown in FIGS. 2A and 2B clearly demonstrates that the hVOR system with impaired time-delay estimation or impaired sensory state predictor can mimic certain outcomes of sensorimotor diseases. However, if the control of hVOR is augmented with a time-delay estimator (FIG. 4) and a predictor for eye position relative to the head, then hVOR control is stable and smooth (see FIGS. 3A and 3B). Specifically, FIGS. 3A and 3B demonstrate the hVOR performance under long time delay (10 ms) simulated using the model provided herein. The hVOR system is stable when the brain model is equipped with time-delay estimator and state predictor.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Abdelghani M, Lillicrap T, Tweed D: Sensitivity derivatives for flexible sensorimotor learning. *Neural computation* 2008, 20(8):2085-2111.
2. Abdelghani M N, Tweed D B: Learning course adjustments during arm movements with reversed sensitivity derivatives. *BMC neuroscience* 2010, 11(1):150.
3. Raibert M H: A model for sensorimotor control and learning. *Biological Cybernetics* 1978, 29(1):29-36.

4. Todorov E, Jordan M I: Optimal feedback control as a theory of motor coordination. *Nature neuroscience* 2002, 5(11): 1226-1235.
5. Franklin D W, Wolpert D M: Computational mechanisms of sensorimotor control. *Neuron* 2011, 72(3):425-442.
6. Matthews P B: The human stretch reflex and the motor cortex. *Trends in neurosciences* 1991, 14(3):87-91.
7. Ito T, Murano E Z, Gomi H: Fast force-generation dynamics of human articulatory muscles. *Journal of applied physiology* 2004, 96(6):2318-2324.
8. Aw S T, Todd M J, Halmagyi G M: Latency and initiation of the human vestibuloocular reflex to pulsed galvanic stimulation. *Journal of neurophysiology* 2006, 96(2):925-930.
9. Abaspour A, Sadati S H, Sadeghi M: Nonlinear optimized adaptive trajectory control of helicopter. *Control Theory and Technology* 2015, 13(4):297-310.
10. Abaspour A, Sadeghi M, Sadati H: Using fuzzy logic in dynamic inversion flight controller with considering uncertainties. In: *13th Iranian Conference on Fuzzy Systems (IFSC)*: 2013.
11. Abaspour A, Parsa N T, Sadeghi M: A New Feedback Linearization-NSGA-II based Control Design for PEM Fuel Cell. *International Journal of Computer Applications* 2014, 97(10).
12. Dallos P, Jones R: Learning behavior of the eye fixation control system. *Automatic Control, IEEE Transactions on* 1963, 8(3):218-227.
13. Stark L, Vossius G, Young L R: Predictive control of eye tracking movements. *IRE Transactions on Human Factors in Electronics* 1962, 2(HFE-3):52-57.
14. Westheimer G: Eye movement responses to a horizontally moving visual stimulus. *AMA Archives of Ophthalmology* 1954, 52(6):932-941.
15. Pavel M: Predictive control of eye movement. *Reviews of oculomotor research* 1989, 4:71-114.
16. Morris E, Lisberger S: Signals used to maintain smooth pursuit eye movements in monkeys: Effects of small retinal position and velocity errors. *Society for Neuroscience Abstract* 1983, 9:866.
17. Morris E, Lisberger S: Different responses to small visual errors during initiation and maintenance of smooth-pursuit eye movements in monkeys. *Journal of Neurophysiology* 1987, 58(6):1351-1369.
18. Churchland M M, Lisberger S G: Apparent motion produces multiple deficits in visually guided smooth pursuit eye movements of monkeys. *Journal of Neurophysiology* 2000, 84(1):216-235.
19. Miall R C, Christensen L O, Cain O, Stanley J: Disruption of state estimation in the human lateral cerebellum. *PLoS biol* 2007, 5(11):e316.
20. Cleveland W S, Parzen E: The estimation of coherence, frequency response, and envelope delay. *Technometrics* 1975, 17(2):167-172.
21. Carter G C: Coherence and time delay estimation. *Proceedings of the IEEE* 1987, 75(2):236-255.
22. Hinich M J, Wilson G R: Time delay estimation using the cross bispectrum. *Signal Processing, IEEE Transactions on* 1992, 40(1):106-113.
23. Holm S, Ottesen G: Bias in the cross spectrum and time delay estimates due to misalignment. *Acoustics, Speech and Signal Processing, IEEE Transactions on* 1986, 34(6):1662-1665.
24. Cabot R C: A note on the application of the Hilbert transform to time delay estimation. *Acoustics, Speech and Signal Processing, IEEE Transactions on* 1981, 29(3):607-609.
25. Chan Y, Hattin R V, Plant J: The least squares estimation of time delay and its use in signal detection. In: *Acoustics, Speech, and Signal Processing, IEEE International Conference on ICASSP'78*: 1978. IEEE: 665-669.
26. Shibata T, Tabata H, Schaal S, Kawato M: A model of smooth pursuit in primates based on learning the target dynamics. *Neural Networks* 2005, 18(3):213-224.
27. Miiller T, Lauk M, Reinhard M, Hetzel A, Luicking C H, Timmer J: Estimation of delay times in biological systems. *Annals of biomedical engineering* 2003, 31(11):1423-1439.
28. Takarae Y, Luna B, Minshew N J, Sweeney J A: Visual motion processing and visual sensorimotor control in autism. *Journal of the International Neuropsychological Society* 2014, 20(01):113-122.
29. Koelewijn L, Hamandi K, Brindley L M, Brookes M J, Routley B C, Muthukumaraswamy S D, Williams N, Thomas M A, Kirby A, te Water Naudé J: Resting-state oscillatory dynamics in sensorimotor cortex in benign epilepsy with centro-temporal spikes and typical brain development. *Human brain mapping* 2015.
30. Sargolzaei A, Yen K K, Abdelghani M N: Preventing Time-Delay Switch Attack on Load Frequency Control in Distributed Power Systems. *IEEE Transactions on Smart Grid* 2016, 7:1176-1185.
31. Sargolzaei A, Yen K K, Abdelghani M: Control of Nonlinear Heartbeat Models under Time-Delay-Switched Feedback Using Emotional Learning Control. *International Journal on Recent Trends in Engineering & Technology* 2014, 10(2).
32. Sargolzaei A, Yen K, Abdelghani M: Delayed inputs attack on load frequency control in smart grid. In: *Innovative Smart Grid Technologies Conference (ISGT), 2014 IEEE PES*: 2014. IEEE: 1-5.
33. Leigh R J, Zee D S: The neurology of eye movements: Oxford University Press; 2015.
34. Kheradmand A, Zee D S: Cerebellum and ocular motor control. *Frontiers in neurology* 2011, 2.

What is claimed is:
1. A method of estimating time delay of a sensorimotor control system in a subject, comprising:
  obtaining Jacobian matrices that respectively describe sensory states G(t) and motor control B(t) of the system;
  obtaining a control vector u(t) describing neural motor commands from a neural network of the subject that dictate a desired motion or task of a muscle of the subject, the desired motion or task being described by a reference trajectory r(t);
  computing a delayed sensory state of the system, described by vector x(t−τ) using the values of G(t), B(t), and u(t);
  estimating, based on G(t), B(t), x(t−τ), and u(t), a time delay τ of the system for performing the desired motion; and
  improving a condition of the subject by stimulating sensory neurons of the subject through transmission, via a transmitting device, of a visual stimulation signal to the sensory neurons of the subject, the visual stimulation signal being generated based upon the estimated time delay, and the visual stimulation signal increasing a speed of the sensory neurons of the subject,
  the computing of the delayed sensory state vector x(t−τ) comprising the use of the following equation:

$$x(t-\tau) = G(t-\tau)x_0 + G(t-\tau)\int_0^{t-\tau} G^{-1}(s)B(s)u(s)ds$$

where $x_0$ is an initial sensory state, and
where t is time and $\tau$ is the actual time delay.

2. A method of estimating time delay of a sensorimotor control system in a subject, comprising:
obtaining Jacobian matrices that respectively describe sensory states G(t) and motor control B(t) of the system;
obtaining a control vector u(t) describing neural motor commands from a neural network of the subject that dictate a desired motion or task of a muscle of the subject, the desired motion or task being described by a reference trajectory r(t);
computing, based on G(t), B(t), and u(t), a delayed sensory state of the system, described by vector x(t–$\tau$);
estimating a time delay $\hat{\tau}$ of the system for performing the desired motion; and
improving a condition of the subject by stimulator sensor neurons of the subject through transmission, via a transmitting device, of a visual stimulation signal to the sensory neurons of the subject, the visual stimulation signal being generated based upon the estimated time delay, and the visual stimulation signal increasing a speed of the sensory neurons of the subject,
the estimating of the time delay comprising the use of the following equation:

$$\frac{d\hat{\tau}}{dt} = \eta\zeta\frac{\partial G(t-\hat{\tau})}{\partial \hat{\tau}}\left[x_0 + \int_0^{t-\hat{\tau}}(B(s)/G(s))u(s)ds\right] - \eta\zeta\{B(t-\hat{\tau})u(t-\hat{\tau}) - G(t-\hat{\tau})B(0)u(0)\}$$

where $\eta$ is a learning parameter,
where $x_0$ is an initial sensory state,
where t is time and $\tau$ is the actual time delay, and
Where $\zeta = x(t-\tau) - x(t-\hat{\tau})$.

3. The method according to claim 2, the computing of the delayed sensory state vector x(t–$\tau$) comprising the use of the following equation:

$$x(t-\tau) = G(t-\tau)x_0 + G(t-\tau)\int_0^{t-\tau} G^{-1}(s)B(s)u(s)ds.$$

4. The method according to claim 1, the subject being a human or a primate.

5. The method according to claim 4, desired motion or task being a horizontal vestibule-ocular reflex, a saccadic eye movement, or a smooth pursuit eye motion.

6. The method according to claim 1, the values of G(t), B(t), and u(t) being stored in the sensorimotor control system for a time period between t and t–$\tau_{max}$, where $\tau_{max}$ is a maximum possible delay after which the sensorimotor control system becomes inoperable.

7. A method of estimating time delay of a sensorimotor control system in a subject, comprising:
obtaining Jacobian matrices that respectively describe sensory states G(t) and motor control B(t) of the system;
obtaining a control vector u(t) describing neural motor commands from a neural network of the subject that dictate a desired motion or task of a muscle of the subject, the desired motion or task being described by a reference trajectory r(t);
computing, based on G(t), B(t), and u(t), a delayed sensory state of the system, described by vector x(t–$\tau$), where t is time and $\tau$ is the actual time delay;
estimating based on G(t), B(t), x(t–$\tau$), and u(t), a time delay $\hat{\tau}$ of the system for performing the desired motion; and
improving, a condition of the subject by stimulating sensory neurons of the subject through transmission, via a transmitting device, of a visual stimulation signal to the sensory neurons of the subject, the visual stimulation signal being generated based upon the estimated time delay, and the visual stimulation signal increasing a speed of the sensory neurons of the subject,
the estimated time delay z being used to predict a future sensory state described by vector $\hat{x}(t)$ using the following equation:

$$\hat{x}(t) = G(t)G^{-1}(t-\hat{\tau})x(t-\hat{\tau}) + G(t)\int_{t-\hat{\tau}}^{t} B(s)G^{-1}(s)u(s)ds.$$

8. The method according to claim 1, further comprising predicting natural physiological delays of the subject, neurological disorders of the subject, and sensory organ disorders of the subject based upon the estimated time delay.

9. The method according to claim 1, further comprising predicting a neurological disorder of the subject based upon the estimated time delay, the neurological disorder being selected from autism, epilepsy, Parkinson's disease, and Alzheimer's disease.

10. A method of predicting the future sensory state of a sensorimotor control system in a subject, comprising:
obtaining Jacobian matrices that respectively describe sensory states G(t) and motor control B(t) of the system;
obtaining a control vector u(t) describing the neural motor commands from a neural network of the subject that dictate a desired motion or task of a muscle of the subject, the desired motion or task being described by a reference trajectory r(t);
computing a delayed sensory state of the system, described by vector x(t–$\tau$) using the values of G(t), B(t), and u(t);
estimating, based on G(t), B(t), x(t–$\tau$), and u(t), a time delay $\hat{\tau}$ of the system for performing the desired motion of task;
predicting the future sensory state of the system described by vector $\hat{x}(t)$; and
improving a condition of the subject by stimulating sensory neurons of the subject through transmission, via a transmitting device, of a visual stimulation signal to the sensory neurons of the subject, the visual stimulation signal being generated based upon the estimated time delay, and the visual stimulation signal increasing a speed of the sensory neurons of the subject,
the computing of the delayed sensory state vector x(t–$\tau$) comprising the use of the following equation:

$$x(t-\tau) = G(t-\tau)x_0 + G(t-\tau)\int_0^{t-\tau} G^{-1}(s)B(s)u(s)ds$$

where $x_0$ is an initial sensory state, and
where t is time and $\tau$ is the actual time delay.

11. A method of predicting the future sensory state of a sensorimotor control system in a subject, comprising:
  obtaining Jacobian matrices that respectively describe sensory states G(t) and motor control B(t) of the system;
  obtaining a control vector u(t) describing the neural motor commands from a neural network of the subject that dictate a desired motion or task of a muscle of the subject, the desired motion or task being described by a reference trajectory r(t);
  computing, based on G(t), B(t), and u(t), a delayed sensory state of the system, described by vector $x(t-\tau)$;
  estimating a time delay of the system for performing the desired motion or task;
  predicting the future sensory state of the system described by vector $\hat{x}(t)$; and
  improving a condition of the subject by stimulating sensory neurons of the subject through transmission, via a transmitting device, of a visual stimulation signal to the sensory neurons of the subject, the visual stimulation signal being generated based upon the estimated time delay, and the visual stimulation signal increasing a speed of the sensory neurons of the subject,
  the estimating of the time delay f comprising the use of the following equation:

$$\frac{d\hat{\tau}}{dt} = \eta\zeta \frac{\partial G(t-\hat{\tau})}{\partial \hat{\tau}}\left[x_0 + \int_0^{t-\hat{\tau}}(B(s)/G(s))u(s)ds\right] - \eta\zeta\{B(t-\hat{\tau})u(t-\hat{\tau}) - G(t-\hat{\tau})B(0)u(0)\}$$

where $x_0$ is an initial sensory state,
  where $\zeta = x(t-\tau) - x(t-\hat{\tau})$,
  where $\eta$ is a learning parameter that represents how fast and effectively the subject learns, and
  where t is time and $\tau$ is the actual time delay.

12. A method of predicting the future sensory state of a sensorimotor control system in a subject, comprising:
  obtaining Jacobian matrices that respectively describe sensory states G(t) and motor control B(t) of the system;
  obtaining a control vector u(t) describing the neural motor commands from a neural network of the subject that dictate a desired motion or task of a muscle of the subject, the desired motion or task being described by a reference trajectory r(t);
  computing, based on G(t), B(t), and u(t), a delayed sensory state of the system, described by vector $x(t-\tau)$, where t is time and $\tau$ is the actual time delay;
  estimating, based on G(t), B(t), $x(t-\tau)$, and u(t), a time delay $\tau$ of the system for performing the desired motion;
  predicting the future sensory state of the system described by vector $\hat{x}(t)$; and
  improving a condition of the subject by stimulating sensory neurons of the subject through transmission, via a transmitting device, of a visual stimulation signal to the sensory neurons of the subject, the visual stimulation signal being generated based upon the estimated time delay, and the visual stimulation signal increasing a speed of the sensory neurons of the subject,
  the predicting of the future sensory state described by vector $\hat{x}(t)$ comprising the use of the following equation:

$$\hat{x}(t) = G(t)G^{-1}(t-\hat{\tau})x(t-\hat{\tau}) + G(t)\int_{t-\hat{\tau}}^{t} B(s)G^{-1}(s)u(s)ds.$$

13. The method according to claim 10, the subject being a human or a primate.

14. The method according to claim 13, the desired motion or task being a horizontal vestibule-ocular reflex, a saccadic eye movement, or a smooth pursuit eye motion.

15. The method according to claim 10, the values of G(t), B(t), and u(t) being stored in the sensorimotor control system for a time period between t and $t-\tau_{max}$, where $\tau_{max}$ is a maximum possible delay after which the sensorimotor control system becomes inoperable.

16. A system for estimating time delay of a sensorimotor control system in a human or primate subject, the system comprising:
  a processor; and
  a computer-readable medium having computer-executable instructions that, when executed by the processor, perform a method of estimating time delay of a sensorimotor control system in a human or a primate subject, the method comprising:
    obtaining Jacobian matrices that respectively describe sensory states G(t) and motor control B(t) of the system;
    obtaining a control vector u(t) describing the neural motor commands from a neural network of the subject that dictate desired motion of a muscle of the subject, the desired motion being described by a reference trajectory r(t);
    computing a delayed sensory state of the system, described by vector $x(t-\tau)$ using the values of G(t), B(t), and u(t);
    estimating, based on G(t), B(t), $x(t-\tau)$, and u(t), a time delay $\tau$ of the system for performing the desired motion; and
    improving a condition of the subject by stimulating sensory neurons of the subject through transmission, via a transmitting device, of a visual stimulation signal to the sensory neurons of the subject, the visual stimulation signal being generated based upon the estimated time delay, and the visual stimulation signal increasing a speed of the sensory neurons of the subject,
  the desired motion being a horizontal vestibule-ocular reflex, a saccadic eye movement, or a smooth pursuit eye movement, and
  the computing of the delayed sensory state vector $x(t-\tau)$ comprising the use of the following equation:

$$x(t-\tau) = G(t-\tau)x_0 + G(t-\tau)\int_0^{t-\tau} G^{-1}(s)B(s)u(s)ds$$

where $x_0$ is an initial sensory state, and
  where t is time and $\tau$ is the actual time delay.

17. The method according to claim 16, the estimating of the time delay comprising the use of the following equation:

$$\begin{aligned}\frac{d\hat{\tau}}{dt} &= -\eta\zeta\frac{\partial[x(t-\tau)-x(t-\hat{\tau})]}{\partial\hat{\tau}}\\ &= \eta e_m\frac{\partial x(t-\hat{\tau})}{\partial\hat{\tau}}\\ &= \eta\zeta\frac{\partial G(t-\hat{\tau})}{\partial\hat{\tau}}\left[x_0+\int_0^{t-\hat{\tau}}(B(s)/G(s))u(s)ds\right]-\\ &\quad \eta\zeta\{B(t-\hat{\tau})u(t-\hat{\tau})-G(t-\hat{\tau})B(0)u(0)\}\end{aligned}$$

where $\eta$ is a learning parameter that represents how fast and effectively the subject learns, and
where $\zeta = x(t-\tau) - x(t-\hat{\tau})$.

* * * * *